United States Patent
Shafirstein et al.

(10) Patent No.: US 6,780,177 B2
(45) Date of Patent: *Aug. 24, 2004

(54) CONDUCTIVE INTERSTITIAL THERMAL THERAPY DEVICE

(75) Inventors: Gal Shafirstein, Little Rock, AR (US); Scott L. Ferguson, Vilonia, AR (US); Milton Waner, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 80 days.

This patent is subject to a terminal disclaimer.

(21) Appl. No.: 10/228,482

(22) Filed: Aug. 27, 2002

(65) Prior Publication Data

US 2004/0044336 A1 Mar. 4, 2004

(51) Int. Cl.$^7$ .............................................. A61B 18/18
(52) U.S. Cl. ...................................... 606/28; 606/29
(58) Field of Search .............................. 606/27–31, 41, 606/42, 45, 47–50; 607/101–102

(56) References Cited

U.S. PATENT DOCUMENTS

| | | | |
|---|---|---|---|
| 4,646,737 A | | 3/1987 | Hussein et al. |
| 4,672,962 A | * | 6/1987 | Hershenson ................. 606/28 |
| 4,691,703 A | | 9/1987 | Auth et al. |
| 4,735,201 A | * | 4/1988 | O'Reilly ...................... 606/28 |
| 4,860,744 A | | 8/1989 | Johnson et al. |
| 4,872,458 A | | 10/1989 | Kanehira et al. |
| 4,949,718 A | | 8/1990 | Neuwirth et al. |
| 5,047,025 A | * | 9/1991 | Taylor et al. .................. 606/31 |
| 5,057,105 A | * | 10/1991 | Malone et al. ................. 606/28 |
| 5,105,808 A | | 4/1992 | Neuwirth et al. |
| 5,159,925 A | | 11/1992 | Neuwirth et al. |
| 5,190,539 A | * | 3/1993 | Fletcher et al. ............... 606/25 |
| 5,191,883 A | | 3/1993 | Lennox et al. |
| 5,345,936 A | | 9/1994 | Pomeranz et al. |
| 5,425,731 A | * | 6/1995 | Daniel et al. ................. 606/28 |
| 5,456,682 A | | 10/1995 | Edwards et al. |
| 5,492,529 A | | 2/1996 | Neuwirth et al. |
| RE35,330 E | | 9/1996 | Malone et al. |
| 5,571,153 A | | 11/1996 | Wallsten |
| 5,586,982 A | * | 12/1996 | Abela .......................... 606/28 |
| 5,810,802 A | | 9/1998 | Panescu et al. |
| 5,860,974 A | | 1/1999 | Abele |
| 5,868,740 A | | 2/1999 | LeVeen et al. |
| 5,891,134 A | | 4/1999 | Goble et al. |
| 5,897,552 A | | 4/1999 | Edwards et al. |
| 6,024,743 A | | 2/2000 | Edwards |
| 6,053,912 A | | 4/2000 | Panescu et al. |
| 6,056,746 A | | 5/2000 | Goble et al. |
| 6,071,280 A | | 6/2000 | Edwards et al. |
| 6,139,570 A | | 10/2000 | Saadat et al. |
| 6,221,071 B1 | | 4/2001 | Sherry et al. |
| 6,258,086 B1 | | 7/2001 | Ashley et al. |
| 6,290,697 B1 | | 9/2001 | Tu et al. |
| 6,293,943 B1 | | 9/2001 | Panescu et al. |
| 6,312,428 B1 | | 11/2001 | Eggers et al. |

OTHER PUBLICATIONS

Neuwirth, R., et al., The Endometrial Ablator: A New Instrument, Obstetrics & Gynecology, vol. 83, No. 5, Part 1, pp. 792–798, May 1994.

* cited by examiner

Primary Examiner—Michael Peffley
(74) Attorney, Agent, or Firm—Ray F. Cox, Jr.

(57) ABSTRACT

An apparatus and method for thermally destroying tumors in which heat is generated by electrical resistance heating conducted to the target tissue. Computerized scanning is used to optimize the geometry of a thermal probe. The probe has a themally conductive tip containing an electrical resistance heating element. The thermally conductive tip is mounted on the end of a fiber that contains the electrical power leads and other electrical leads connecting to monitoring devices associated with the tip. The tip is coated with a thin layer of biocompatible ceramic to avoid coagulated tissue sticking to the tip. The tip has one or more thin, thermally-conductive elements which deploy in stages to coagulate the tumor. The conductive elements may be thin wires or blades. On one embodiment, the conductive elements are composed of a shape memory material that is folded against the tip at lower temperatures and deploys at selected higher temperatures. In another embodiment, the conductive elements are blades that are deployed mechanically. The tip may be provided with a miniature thermocouple to provide temperature feedback information. The resistance heating element may be pyrolytic graphite.

35 Claims, 6 Drawing Sheets

FIG. 8

CONDUCTIVE INTERSTITIAL THERMAL THERAPY DEVICE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to methods and devices for treating body tissues such as tumors or lesions with thermal energy, and in particular, to such methods and devices that deploy thermally conductive elements to treat a predetermined shape of tissue.

2. Brief Description of the Related Art

Within the last ten years, interstitial thermal therapy of tumors has become an accepted method for treating cancerous tumors. These minimally invasive therapeutic procedures are used to kill cancer tumors without damaging healthy tissues surrounding it. Increasing the temperature of the tumor above a threshold level of about 70–130 C will cause tumor death. Interstitial thermal devices for thermal tissue ablation including radio frequency ablation (RFA), microwave and laser based technologies have been developed and have received 510K FDA clearance. All of these techniques use radiation to transfer the energy to the tumor, and therefore the heat in the tumor is generated indirectly through local energy absorption sites (e.g., blood in the case of a laser or fat in the case of RFA) could result in a non-homogenous heating of the tumor. The consequences of a non-uniform heating of the tumor could include incomplete death of the tumor and/or skin burns and injury of healthy tissues or organs. Incomplete tumor death will result in recurrence of multiple small tumors in the treated area.

Moreover, as most of the heat is transfer by radiation (in laser, RFA and microwave), it is very difficult to calculate the temperature distribution without precisely knowing the fine microstructure (down to the cell level) that cannot be predetermined with a non-invasive method. In addition the temperature measurements are also challenging; in these cases, since the probes could be directly heated by the energy sources and will show it's own temperature rather than that of the tissue. For example, in laser or RFA thermocouples may get hot from the source much quicker than tissue (as they absorb RF and laser energy more than tissue) and will show temperatures that are higher than the actual temperature in the lesion. That could result in insufficient heating and if the operator increases the amount of energy delivered to the tumor, an overheating may occur which will result in burning. Another limitation of RFA is that it is not MRI-compatible.

The limitations of the prior art are overcome by the present invention as described below.

BRIEF SUMMARY OF THE INVENTION

The present invention is an alternative to Laser Interstitial Thermal Therapy (LLIT) and RFA, which is used to destroy tumors or lesions through the absorption of radiation by tissue. However, as discussed above, in the LLIT and RFA processes, the temperature cannot be predicted or easily controlled due to the varying light and RF energy absorption properties of different types of tissue. In addition, RFA will interfere with implants (such as pacemakers) and the patient with such implants cannot be treated with RFA.

The present invention also destroys tumors thermally, but the heat is generated directly by electrical resistance heating conducted to the tissue rather than through the absorption of non-ionized radiation by the tissue. The process of the present invention involves computerized scanning (CAT, CT, PET, or MRI) to mathematically determine the location and shape of the tumor. The information derived from the scan allows a stereotactic frame or other technique such as ultrasound to be used to position a probe within the tumor.

The probe comprises a thermally conductive tip containing an electrical resistance heating element. The thermally conductive tip is mounted on the end of a fiber which is separated from the tip by a heat sink to avoid thermal conduction down the fiber. The fiber contains the electrical power leads and other electrical leads connecting to monitoring devices associated with the tip. The tip is coated with a thin biocompatible coating, such as diamond-like coating, ceramic, polymers and the like, to avoid coagulated tissue sticking to the tip.

The area of tissue treated by the tip is determined by the addition of one or more thin, thermal conductive elements, which may be formed of shape memory material, such as nitinol. The shape memory elements are desirably in the form of thin wires or pins which are folded against the tip at lower temperatures and which deploy at selected higher temperatures. The shape memory elements may be deployed in multiple stages at succesively higher temperatures so that succesive layers of the tumor are exposed to specific temperatures during treatment. Coagulating the tumor in succesive layers is desirable to avoid hemoraging. By selecting the number, size and placement of the shape memory elements, tumors of varying sizes and shapes may be treated in a predictable, controllable fashion.

In order to control the process, the tip may also be provided with a miniature thermocouple or the like to provide temperature feedback information to control the temperature of the tip. Through knowledge of the shape and location of the tumor obtained from computerized imaging, the design of the tip and shape memory elements, and the temperature feedback information, information can be presented to the operator showing the specific progress of the treatment of a tumor and allowing predictable control of the process.

In alternative embodiments, deployable pivoted razorblades rather than thin wires are employed to conduct the thermal energy to the tumor. The razorblades are deployed mechanically rather than being deployed due to temperature dependent shape memory effects. In one embodiment, a linear actuator, comprising a threaded shaft operated by a motor, deploys the razorblade thermal conductive elements. In another embodiment, a nitinol spring is heated so as to extend and deploy the razorblade elements.

In all embodiments, a pyrolytic graphite element may be used to provide the heat source. Pyrolytic graphite has unique thermal properties in that it acts as a resistor axially but is conductive radially.

In a further embodiment, the deployable razorblades are deployed mechanically by a spring-biased copper conductor that serves a dual function—as a plunger to push deploying arms on the razorblades and also as a conductor for the power supply for the pyrolytic graphite heater element. The plunger is housed in a shaft which is coated with an electrically conductive material, for example, gold, to act as the power return or ground so as to complete the electrical circuit supplying power to the heater element. When the plunger moves forwardly to push the arms on the razorblades, it may also extend a needle which helps to hold the probe in place when the razorblades deploy.

The deployable razorblades may be deployed in stages to treat the tumor layer by layer. The deployment may be triggered at specified temperatures as measured by temperature feedback elements in the probe tip.

The present invention uses thermal conduction, as opposed to radiation absorption, to heat the tumor/lesion volume. Since the thermal properties of tissue are relatively homogenous, the results can be predicted. The shape of the probe tip in the form of the deployable thermal conductive elements may be altered during treatment. The combination of shape and activation temperature can be predetermined for any specific tumor/lesion geometry. This offers the following advantages: highly predictable temperature distribution; larger areas can be effectively treated, in a controlled manner, since the heat is dissipated primarily by conduction; localized carbonization will not result in tunneling and the process is safer than LLIT or RFA; the maximum temperature in the treatment zone will never exceed the temperature at the tip of the probe, and therefore, one can easily control the maximum temperature within the tumor/lesion and adjacent tissues; temperature may be actively controlled via closed loop feedback system, where the maximum temperatures are measured during the process by placing miniature thermocouples at the end of the thermal probe.

These and other features, objects and advantages of the present invention will become better understood from a consideration of the following detailed description of the preferred embodiments and appended claims in conjunction with the drawings as described following.

BRIEF DESCRIPTION OF THE SEVERAL VIEWS OF THE DRAWINGS

FIGS. 1A, 1B and 2 are views of an embodiment of the present invention in which the deployable thermal conductive elements are shape memory wires.

FIGS. 3–5 are views of an alternative embodiment of the present invention in which the deployable thermal conductive elements are pivoted razorblades deployed by a linear actuator.

FIGS. 9 and 10 are views of an embodiment of the present invention in which the deployable thermal conductive elements are shape memory wires in the form of coils.

FIGS. 11A and 11B are sectional views of an alternative embodiment of the embodiment of FIG. 7 wherein the deployed razorblades are spring biased to aid in retraction of the razorblades from the deployed position.

DETAILED DESCRIPTION OF THE INVENTION

With reference to FIGS. 1A–10, the preferred embodiments of the present invention may be described as follows.

The present invention is a miniature thermal apparatus for the controlled destruction of malignant and benign tumors/lesions. As used herein, the terms tumors and lesions may be used interchangeably to indicate tissue to be thermally treated by the device and method of the present invention. The present invention comprises a tip 10 mounted onto a fiber 11 that can be inserted through a catheter that has been accurately placed within the tumor/lesion. The tumor/lesion is destroyed via heat generation originating from the specifically designed tip 10 that matches the tumor/lesion geometry. The tip 10 comprises a plurality of deployable thermal conductive elements that may be customized by the number, size and arrangement to be deployable into a geometry that matches the geometry of the tumor/lesion to be thermally treated. The temperature distribution around the tip 10, within the tumor/lesion and in the adjacent tissue may be predicted by mathematical models of the heat transfer equations. Software may be employed in conjunction with the mathematical models of the heat transfer to provide (1) process monitoring and control, (2) custom probe design, and (3) process simulation. Additionally, using this predictive ability, the process may be monitored and controlled with a closed loop feedback system utilizing sensors in the tip 10. The geometry of the tip 10 may be changed as a function of temperature to increase the volume of irreversibly damaged tissue in the tumor/lesion.

Figure 8:
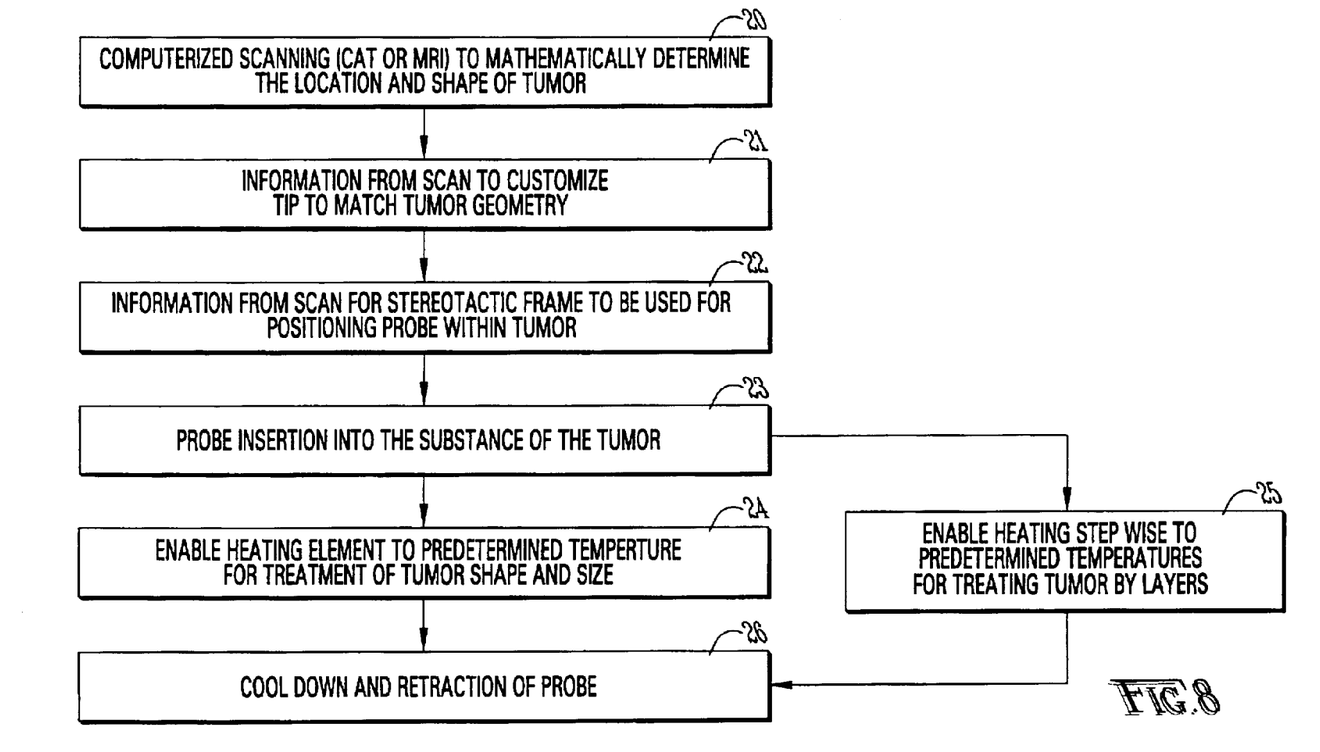
FIG. 8 is a block diagram of the method of the present invention.

As shown in FIG. 8, the process of the present invention involves the step of computerized scanning (CAT, CT, PET, or MRI) to mathematically determine the location and shape of the tumor 20. The information derived from the scan allows the geometry of the tip to be customized to treat the specific shape of the tumor 21 and also allows a stereotactic frame to be used to position the probe within the tumor 22. Ultrasound or the like may be also used to position the probe. The probe is inserted into the tumor 23, and the heating element is activated to a predetermined temperature to treat the tumor 24. Alternatively, the temperature may be increased in a stepwise fashion to treat the tumor in layers 25. Finally, the probe is cooled and withdrawn from the treated tumor 26. As an adjunct to the treatment process, the coagulation of the tumor may be enhanced by the use of a drug effective in reducing bleeding from vascular damage, such as NovoSeven (recombinant factor VIIa) or other coagulant enhancement drug such as Aminocaproic acid (Amicar). NovoSeven is used to stop bleeding in various surgical procedures. The drug is delivered systemically but only works in regions of the body in which vascular damage has taken place. In the procedure of the present invention, the drug would be administered approximately ten minutes prior to the procedure. Thereafter, the apparatus of the present invention is introduced into the tumor. Once the temperature of the tissue has increased to the point that the endothelial cells in the blood vessels are damaged, coagulation is initiated by NovoSeven in the areas of the damaged vessels. The process aids in heat transfer and may aid in the destruction of the tumor by nutrient deprivation. An ancillary advantage to using NovoSeven is that it will decrease the risk of bleeding along the track of the apparatus. The drug is metabolized in about two hours.

The thermally conductive tip 10 contains an electrical resistance heating element 13. The thermally conductive tip 10 is mounted on the end of fiber 11 which is separated from the tip 10 by a heat sink 12 to avoid thermal conduction down the fiber 11. The fiber 11 contains the electrical power leads 14 and may also contain other electrical leads connecting to monitoring devices associated with the tip 10. The tip 10 is coated with a thin biocompatible coating 15 to avoid coagulated tissue sticking to the tip 10. The thin biocompatible coating 15 may be diamond-like coatings, ceramic, polymers and the like.

Figures 1A, 1B:
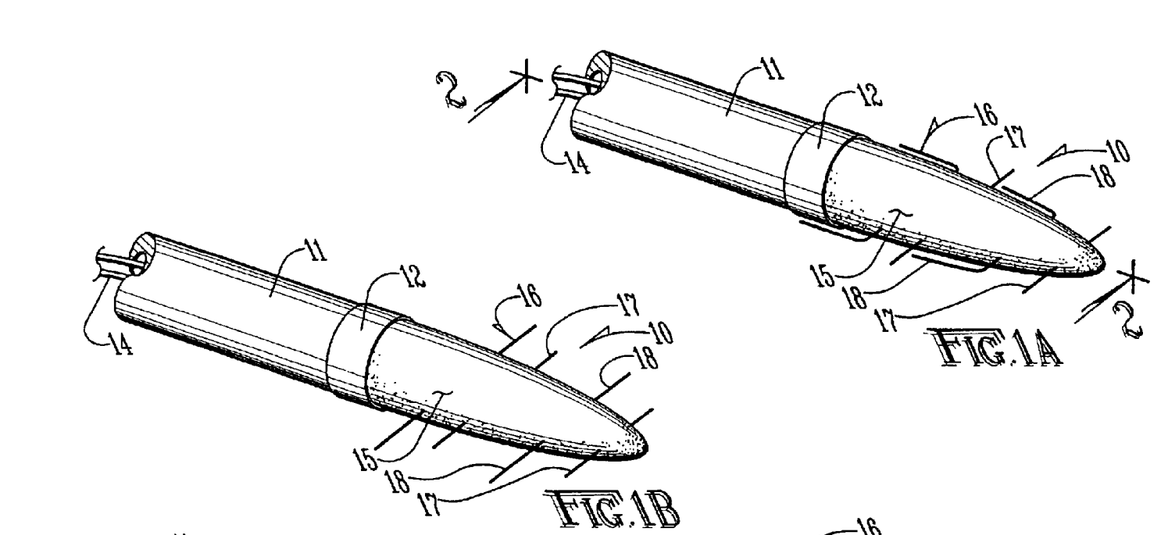
FIG. 1A is a perspective view showing the first stage deployment of the shape memory wires.
FIG. 1B shows the second stage deployed.
Figure 2:
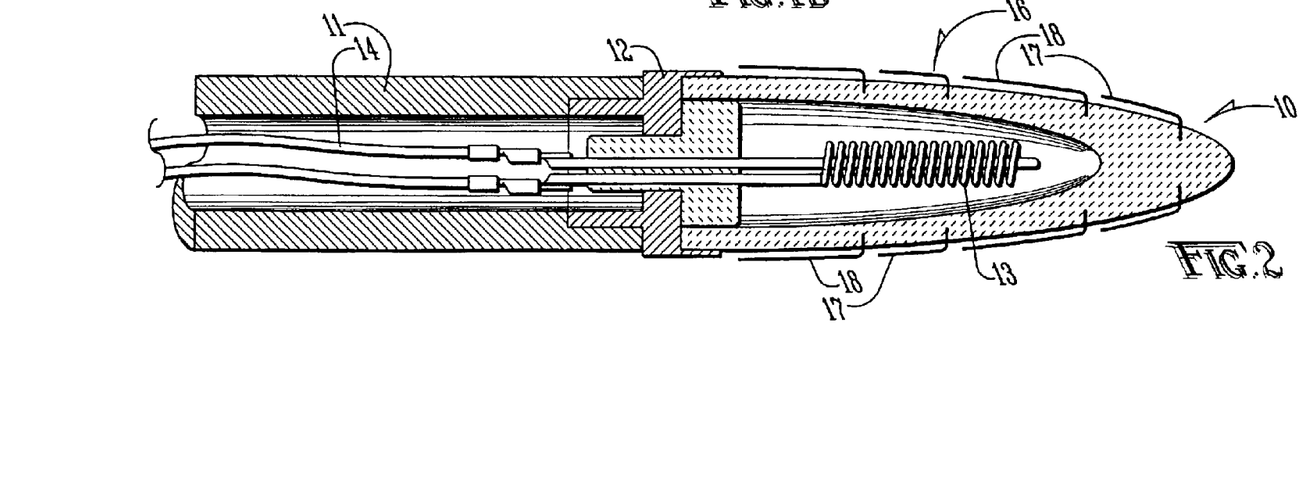
FIG. 2 is a sectional view of the device of FIGS. 1A and 1B along the lines 2—2 of FIGS. 1A and 1B with the shape memory wires in the non-deployed configuration.
Figures 3, 4, 5:
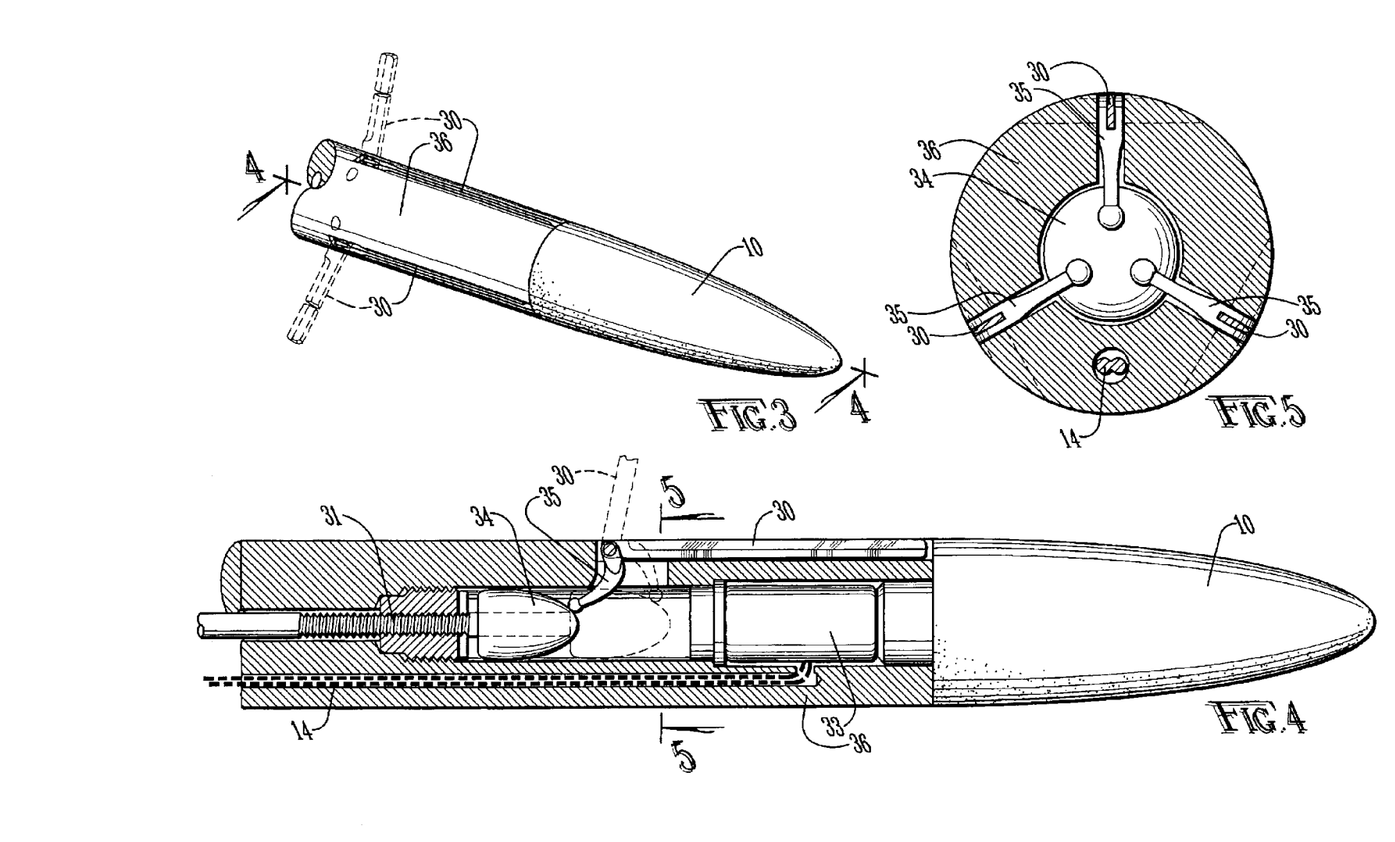
FIG. 3 is a perspective view of the present invention in which the pivoted razorblades are shown by broken lines in the deployed configuration.
FIG. 4 is a sectional view along the line 3—3 of FIG. 3.
FIG. 5 is a sectional view along the line 5—5 of FIG. 3.
Figure 6:
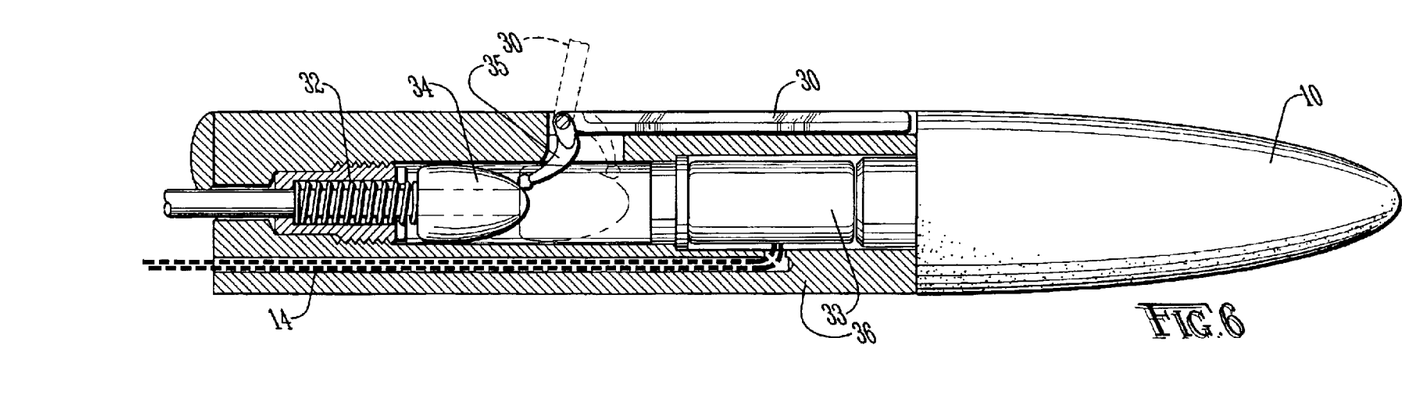
FIG. 6 is a sectional view of a further alternative embodiment of the present invention in which the deployable thermal conductive elements are pivoted razorblades deployed by a nitinol muscle wire.

The area of tissue treated by the tip 10 can be adjusted by the addition of one or more deployable, thermal conductive elements. The deployable elements may be shape memory elements 16 made of shape memory materials, such as nitinol. The shape memory elements 16 are desirably in the form of thin wires or pins which are folded against the tip 10 at lower temperatures as shown in FIG. 2 and which deploy at selected higher temperatures. The shape memory elements 16 may be deployed in multiple stages at succesively higher temperatures so that succesive layers of the tumor are exposed to specific temperatures during treatment. For example, a set of short shape memory elements 17 may be deployed at a first temperature and a set of longer shape memory elements 18 may be deployed at a higher second temperature. Coagulating the tumor in successive layers is desirable to avoid hemoraging. By selecting the number, size and placement of the shape memory elements 16, tumors of varying sizes and shapes may be treated in a predictable, controllable fashion.

In order to control the process, the tip 10 may also be provided with a miniature thermocouple to provide temperature feedback information to control the temperature of the tip 10. Through knowledge of the shape and location of the tumor obtained from computerized imaging, the design of the tip 10 and shape memory elements 16, and the temperature feedback information, information can be presented to the operator showing the specific progress of the treatment of a tumor and allowing predictable control of the process.

Figure 9:
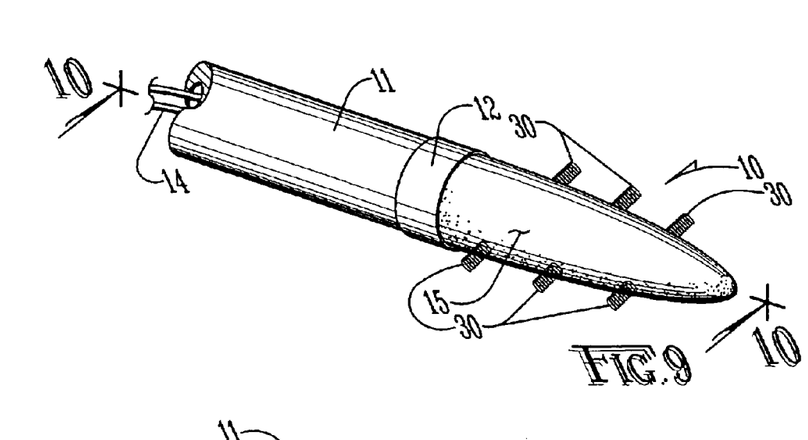
FIG. 9 is a perspective view showing the deployment of the shape memory wires.
Figure 10:
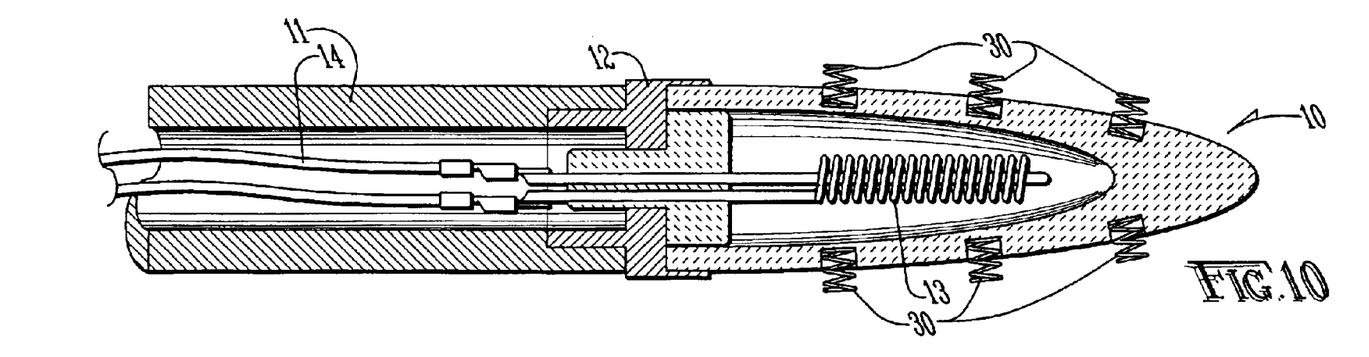
FIG. 10 is a sectional view of the device of FIG. 9 along the lines 10—10 with the shape memory wires in the non-deployed configuration.

As shown in FIGS. 9 and 10, an alternative design of shape memory elements 30 employs shape memory material, such as nitinol, in the form of coils which expand to a deployed configuration as shown in FIG. 9 from a non-deployed configuration as shown in FIG. 10.

Alternative embodiments as shown in FIGS. 3–7 use deployable pivoted razorblades 30 rather than thin shape memory wires as the thermal conductive elements to conduct the thermal energy to the tumor. Desirably, the pivoted razorblades 30 may be made of biocompatible materials, such as composite materials including aluminum silicon carbide, titanium boride and the like. The pivoted razorblades 30 may be deployed mechanically rather than being deployed by a nitinol shape memory wire element. In one embodiment shown in FIG. 4, a linear actuator, comprising a threaded shaft 31 operated by a motor (not shown), deploys the razorblade 30. In another embodiment shown in FIG. 6, a nitinol spring 32 is heated so as to extend and deploy the razorblade elements 30. In both embodiments, a pyrolytic graphite element 33 may be used to provide the heat source. Pyrolytic graphite has unique thermal properties in that it acts as a resistor axially but is conductive radially.

Figure 7:
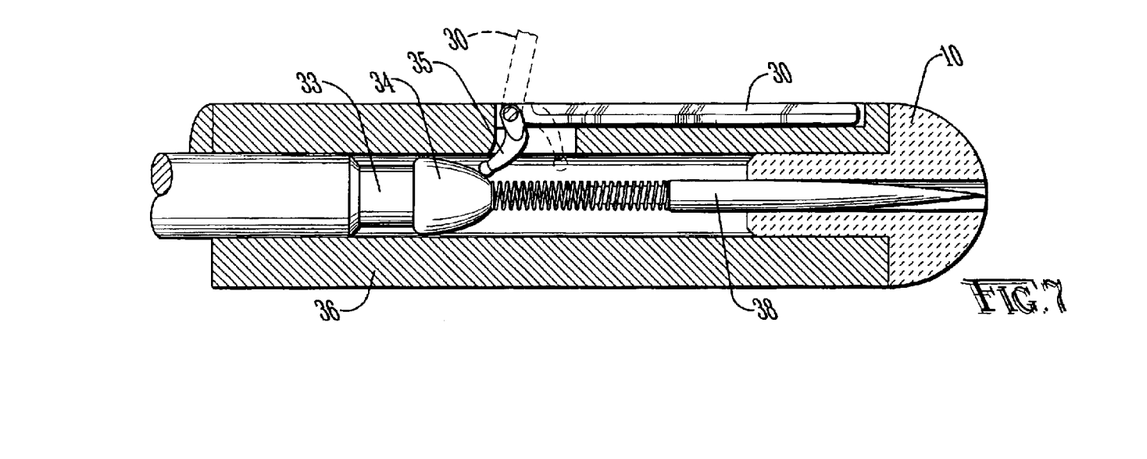
FIG. 7 is a sectional view of a further alternative embodiment of the present invention in which the deployable thermal conductive elements are pivoted razorblades deployed by a plunger. The activation of the plunger also deploys a needle through the forward end of the tip.

In a further embodiment shown in FIG. 7, the deployable razorblades 30 are deployed mechanically by a spring-biased copper conductor that serves as a plunger 34 to push deploying arms 35 on the razorblades 30. The plunger 34 also acts as a conductor for the power supply for the pyrolytic graphite heater element 33. The copper conductor is housed in a shaft 36 which is coated with an electrically conductive material such as gold to act as the power return or ground so as to complete the electrical circuit supplying power to the heater element 33. When the copper conductor plunger 34 moves forwardly to push the arms 35 on the razorblades 30, it may also extend a needle 36 which helps to hold the probe in place when the razorblades 30 deploy.

Figure 11A:
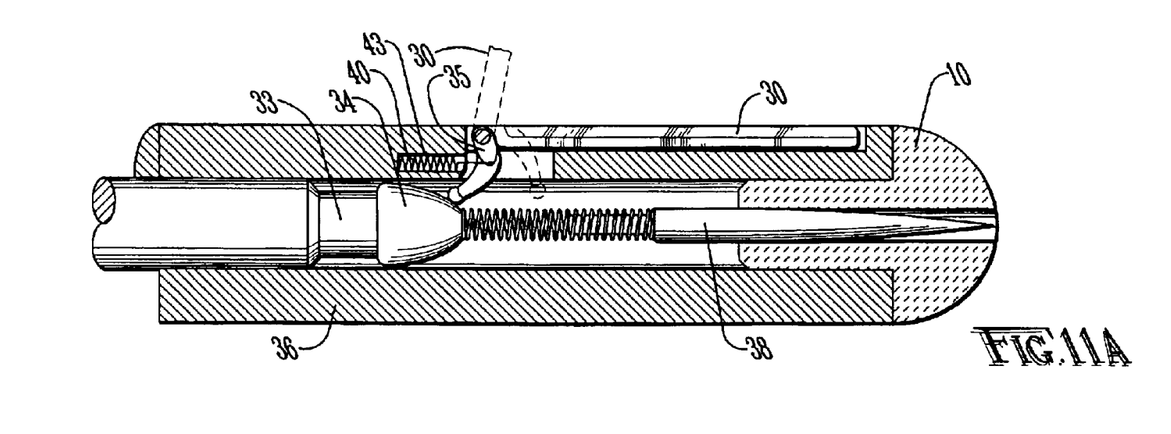
FIG. 11A is an embodiment in which the biasing spring is located to the proximal side of the probe and FIG. 11B is an embodiment in which the biasing spring is located to the distal side of the probe.
Figure 11B:
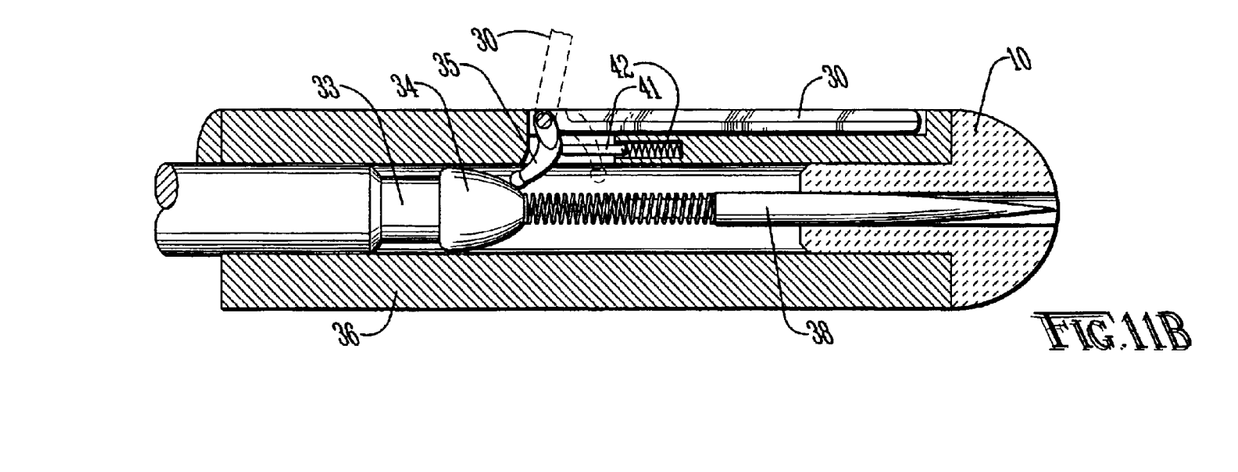

FIGS. 11A and 11B are sectional views of an alternative embodiment of the embodiment of FIG. 7 wherein the deployed razorblades 30 are biased by spring 40, 42 to aid in retraction of the razorblades 30 from the deployed position. FIG. 11A is an embodiment in which biasing spring 40 is located to the proximal side of tip 10. Spring 40 is fixed at one end in a bore 43 and at the other end to deploying arm 35. As razorblade 30 is extended, spring 40 also extends and exerts a force tending to retract razorblade 30. FIG. 11B is an embodiment in which the biasing spring 42 is located to the distal side of tip 10. Spring 42 bears against pin 41 which in turn bears against deploying arm 35. As razorblade 30 is deployed, spring 42 is compressed and thereby exerts a force tending to retract razorblade 30. Biasing springs 40, 42 may also be used in the embodiments of FIGS. 4 and 6 as well as FIG. 7.

The main limitations of the present invention are that the heating process is not selective and the device may require increasing the minimum size of the catheter since the tip 10 of the probe may be larger than a standard laser tip.

These limitations are not serious, however. Even though the heating process is not selective, the device of the present invention may be used effectively to treat tumors where the surrounding area needs to be destroyed (e.g. malignant tumors). Although the size of the thermal tip 10 is expected to be larger than a standard laser tip, the maximum size could be limited to 1.6–5 mm in diameter, which is still acceptable for interstitial procedures. Also, the size of the tip 10 could be reduced to LITT size, by using a laser as an energy source to heat up a metal tip 10.

The present invention has been described with reference to certain preferred and alternative embodiments that are intended to be exemplary only and not limiting to the full scope of the present invention as set forth in the appended claims.

What is claimed is:

1. An apparatus for the thermal treatment of tissues, comprising:
   a hollow fiber having an end;
   a tip mounted to said end of said hollow fiber;
   heating means for generating heat by electrical resistance, said heating means disposed within said tip;
   power means for connecting said heating means to a source of electrical power; and
   deployable thermal conductive means operatively connected to said tip for conduction of heat generated by said heating means.

2. The apparatus of claim 1 further comprising temperature feedback means associated with said tip for generating a signal proportional to a temperature of said tip and signal transmission means for connecting said temperature feedback means to temperature display means.

3. The apparatus of claim 1 further comprising a non-stick biocompatible coating on said tip.

4. The apparatus of claim 1 further comprising heat sink means associated with said tip for avoiding heat conduction from said tip to said fiber.

5. The apparatus of claim 1 wherein said heating means comprises a pyrolytic graphite element.

6. The apparatus of claim 1 wherein said tip has a surface and said deployable thermal conductive means comprises at least one deployable thermally conductive element having a first configuration in close proximity to said surface of said tip and a second configuration deployed substantially outwardly from said surface of said tip.

7. The apparatus of claim 6 wherein said deployable thermal conductive means further comprises at least one second stage deployable thermally conductive element having a third configuration in close proximity to said surface of said tip and a fourth configuration deployed substantially outwardly from said surface of said tip.

8. The apparatus of claim 6 wherein said deployable thermally conductive element comprises a shape memory wire element having said first configuration at a first temperature and said second configuration at a second temperature.

9. The apparatus of claim 7 wherein said second stage deployable thermal conductive element comprises a shape memory wire element having said third configuration at a third temperature and said fourth configuration at a fourth temperature.

10. The apparatus of claim 6 wherein said deployable thermally conductive means comprises at least one razorblade element pivotally connected to said tip and deploying means for deploying said razorblade element from said first configuration to said second configuration.

11. The apparatus of claim 7 wherein said second stage deployable thermally conductive means comprises at least one razorblade element pivotally connected to said tip and deploying means for deploying said razorblade element from said third configuration to said fourth configuration.

12. The apparatus of claims 10 or 11 wherein said razorblade element comprises a lever arm disposed within said tip whereby motion of said lever arm deploys said razorblade element.

13. The apparatus of claim 12 wherein said deploying means comprises a rod threadedly disposed within said fiber and bearing on said lever arm, and electric motor means operatively connected to said rod for advancing said rod against said lever arm to deploy said razorblade element.

14. The apparatus of claim 12 wherein said deploying means comprises a nitinol muscle spring disposed within said tip and bearing against said lever arm, and means for heating said muscle spring whereby heating of said muscle spring expands said muscle spring to deploy said razorblade element.

15. The apparatus of claim 12 wherein said deploying means comprises a plunger slidably received in said fiber and bearing against said lever arm whereby advancement of said plunger deploys said razorblade element.

16. The apparatus of claim 14 wherein said plunger is electrically conductive and said fiber comprises an electrically conductive outer surface and said power means comprises a circuit comprising said plunger, said electrically conductive outer surface and means connecting said plunger and said outer surface to said heating means to form an electrical circuit for delivering power to said heating means.

17. The apparatus of claims 8 or 9 wherein said shape memory wire comprises nitinol.

18. A method for the thermal treatment of a tumor, comprising, the steps of:
    (a) imaging the tumor by a computerized scan;
    (b) utilizing the computerized scan information to provide an electrical resistance heated tip having a plurality of deployable thermal conductive elements whose deployed shape matches the geometry of the scanned tumor and which deploy at a predetermined temperature;
    (c) utilizing the computerized scan information for positioning the tip into the tumor;
    (d) inserting the tip into the scanned tumor;
    (e) heating the tip to the predetermined temperature to deploy the thermal conductive elements and maintaining the tip in the tumor for a sufficient period of time to substantially destroy the tumor; and
    (f) removing the tip from the tumor.

19. The method of claim 18 wherein the deployable thermal conductive elements of step (b) deploy in stages at stepwise higher temperatures to treat successively larger areas of the tumor.

20. A method for the thermal treatment of a tumor, comprising, the steps of:
    (a) imaging the tumor by a computerized scan;
    (b) utilizing the computerized scan information to provide an electrical resistance heated tip having a plurality of deployable thermal conductive elements whose deployed shape matches the geometry of the scanned tumor;
    (c) utilizing the computerized scan information for positioning the tip into the tumor;
    (d) inserting the tip into the scanned tumor;
    (e) deploying the thermal conductive elements;
    (f) heating the tip to a predetermined temperature and maintaining the tip in the tumor for a sufficient period of time to substantially destroy the tumor; and
    (g) removing the tip from the tumor.

21. An apparatus for the thermal treatment of tissues, comprising:
    a hollow fiber having an end;
    a tip mounted to said end of said hollow fiber;
    heating means for generating heat by electrical resistance, said heating means disposed within said tip;
    power means for connecting said heating means to a source of electrical power; and
    deployable thermal conductive means operatively connected to said tip for conduction of heat generated by said heating means;
    wherein said tip has a surface and said deployable thermal conductive means comprises at least one deployable thermally conductive element having a first configuration in close proximity to said surface of said tip and a second configuration deployed substantially outwardly from said surface of said tip; and
    wherein said deployable thermal conductive means further comprises at least one second stage deployable thermally conductive element having a third configuration in close proximity to said surface of said tip and a fourth configuration deployed substantially outwardly from said surface of said tip.

22. The apparatus of claim 21 wherein said deployable thermally conductive element comprises a shape memory wire element having said first configuration at a first temperature and said second configuration at a second temperature.

23. The apparatus of claim 22 wherein said second stage deployable thermal conductive element comprises a shape memory wire element having said third configuration at a third temperature and said fourth configuration at a fourth temperature.

24. The apparatus of claim 21 wherein said deployable thermally conductive means comprises at least one razorblade element pivotally connected to said tip and deploying means for deploying said razorblade element from said first configuration to said second configuration.

25. The apparatus of claim 24 wherein said second stage deployable thermally conductive means comprises at least one razorblade element pivotally connected to said tip and deploying means for deploying said razorblade element from said third configuration to said fourth configuration.

26. The apparatus of claims 24 or 25 wherein said razorblade element comprises a lever arm disposed within said tip whereby motion of said lever arm deploys said razorblade element.

27. The apparatus of claim 26 wherein said deploying means comprises a rod threadedly disposed within said fiber and bearing on said lever arm, and electric motor means operatively connected to said rod for advancing said rod against said lever arm to deploy said razorblade element.

28. The apparatus of claim 26 wherein said deploying means comprises a nitinol muscle spring disposed within said tip and bearing against said lever arm, and means for heating said muscle spring whereby heating of said muscle spring expands said muscle spring to deploy said razorblade element.

29. The apparatus of claim 26 wherein said deploying means comprises a plunger slidably received in said fiber and bearing against said lever arm whereby advancement of said plunger deploys said razorblade element.

30. The apparatus of claim 29 wherein said plunger is electrically conductive and said fiber comprises an electrically conductive outer surface and said power means comprises a circuit comprising said plunger, said electrically conductive outer surface and means connecting said plunger and said outer surface to said heating means to form an electrical circuit for delivering power to said heating means.

31. The apparatus of claims 22 or 23 wherein said shape memory wire comprises nitinol.

32. The apparatus of claim 21 further comprising temperature feedback means associated with said tip for generating a signal proportional to a temperature of said tip and signal transmission means for connecting said temperature feedback means to temperature display means.

33. The apparatus of claim 21 further comprising a non-stick biocompatible coating on said tip.

34. The apparatus of claim 21 further comprising heat sink means associated with said tip for resisting heat conduction from said tip to said fiber.

35. The apparatus of claim 21 wherein said heating means comprises a pyrolytic graphite element.

* * * * *